(12) United States Patent
Roser et al.

(10) Patent No.: US 6,517,860 B1
(45) Date of Patent: Feb. 11, 2003

(54) METHODS AND COMPOSITIONS FOR IMPROVED BIOAVAILABILITY OF BIOACTIVE AGENTS FOR MUCOSAL DELIVERY

(75) Inventors: Bruce J. Roser, Cambridge (GB); Ian Sanderson, Hertfordshire (GB); Jaap Kampinga, Groningen (NL); Camilo Colaco, Cambridge (GB)

(73) Assignee: Quadrant Holdings Cambridge, Ltd. (GB)

( * ) Notice: Subject to any disclaimer, the term of this patent is extended or adjusted under 35 U.S.C. 154(b) by 0 days.

(21) Appl. No.: 09/000,857

(22) Filed: Dec. 30, 1997

Related U.S. Application Data
(60) Provisional application No. 60/033,976, filed on Dec. 31, 1996.

(51) Int. Cl.[7] .................................. A61F 13/00
(52) U.S. Cl. ................ 424/434; 424/45; 424/450; 514/53; 514/958; 536/119
(58) Field of Search .................. 424/45, 434, 450; 536/119; 514/53, 958

(56) References Cited

U.S. PATENT DOCUMENTS

| | | | |
|---|---|---|---|
| 4,407,786 A | | 10/1983 | Drake et al. ............... 424/14 |
| 4,684,719 A | | 8/1987 | Nishikawa et al. ......... 536/119 |
| 4,793,997 A | | 12/1988 | Drake et al. ............... 424/426 |
| 5,006,343 A | * | 4/1991 | Benson et al. ............. 424/450 |
| 5,011,678 A | | 4/1991 | Wang et al. ................ 424/45 |
| 5,270,048 A | | 12/1993 | Drake ........................ 424/426 |
| 5,591,453 A | | 1/1997 | Ducheyne et al. ......... 424/484 |
| 5,607,915 A | * | 3/1997 | Patton ....................... 514/12 |
| 5,744,155 A | * | 4/1998 | Friedman et al. .......... 424/434 |
| 5,747,001 A | * | 5/1998 | Weidmann et al. ........ 424/45 |

FOREIGN PATENT DOCUMENTS

| | | |
|---|---|---|
| EP | 0 504 760 A1 | 9/1992 |
| EP | 0 577 544 A1 | 1/1994 |
| EP | 0 267 050 B1 | 9/1994 |
| GB | 2257359 A | 1/1993 |
| GB | 2257359 * | 10/1993 |
| WO | WO 90/11756 | 10/1990 |
| WO | 96/03978 * | 2/1996 |

OTHER PUBLICATIONS

Product information from Mentholatum Company.
Akoh et al., "One–stage synthesis of raffinose fatty acid polyesters" *J. Food Sci.* (1987) 52:1570–1576.
Arima et al., "Effect of inhaled cyclosporin A on the allergen induced late asthmatic response and increased in airway hyperresponsiveness in a guinea pig model of asthma" *Jpn. J. Allergol.* (1994) 43:1316–1325.
Bangham et al.,, "The physical properties of an effective lung surfactant" *Biochim. Biophys. Acta* (1979) 573:552–556.
Khan, "Chemistry and new uses of sucrose: How important?" *Pure & Appl. Chem.* (1984) 56:833–844.
Khan et al., "Cyclic acetals of 4,1',6'–trichloro–4,1',6'–trideoxy–galacto–sucrose and their conversion into methyl ether derivatives" *Carbohyd. Res.* (1990) 198:275–283.

(List continued on next page.)

Primary Examiner—Thurman K. Page
Assistant Examiner—Lakshmi Channavajjala
(74) Attorney, Agent, or Firm—Saliwanchik, Lloyd & Saliwanchik

(57) ABSTRACT

The invention encompasses compositions for increased bioavailability through mucosal delivery comprising, preferably in powder form, an intimate mixture of an effective amount of a bioactive agent and a hydrophobically derivatized carbohydrate. The compositions can also contain a surface active agent preferably for delivery to gastrointestinal mucosa and ocular delivery.

30 Claims, 9 Drawing Sheets

OTHER PUBLICATIONS

Khan et al. "Enzymic regioselective hydrolysis of peracetylated reducing disaccharaides, specifically at the anomeric centre: Intermediates for the synthesis of oligosaccharides" *Tetra. Ltrs.* (1993) 34:7767–7770.

Tominaga et al., "A similarity and a difference between two models of late eosinophil accumulation into the airway induced by antigen exposure in actively sensitized brown Norway (BN) rats" *Gen. Pharmac.* (1995) 26:353–356.

* cited by examiner

METHODS AND COMPOSITIONS FOR IMPROVED BIOAVAILABILITY OF BIOACTIVE AGENTS FOR MUCOSAL DELIVERY

CROSS-REFERENCE TO RELATED APPLICATIONS

This application claims the benefit of U.S. Provisional Application No. 60/033,976, filed Dec. 31, 1996.

TECHNICAL FIELD

This invention relates to compositions for use in delivery of bioactive agents to mucosal surfaces. The compositions provide increased bioavailability of the bioactive agents, particularly hydrophobic bioactive agents.

BACKGROUND ART

Oral delivery is the potentially most attractive route of bioactive agent delivery as it involves non-invasive techniques and enjoys a high patient compliance. The main drawback with oral delivery is the poor bioavailability of the vast majority of molecules via the gastrointestinal mucosa. Bioavailability refers to both the true rate and total amount (extent) of drug that reaches the general circulation from an administered dosage form.

Bioavailability is limited mainly by the dissolution and stability of the macromolecule in the milieu at the mucosal surface and the transport of the macromolecule across this surface (during absorption). While the former favours hydrophilic bioactive agents with increased dissolution in aqueous body fluids at the mucosal surface, the latter favours hydrophobic molecules which need to cross the apolar lipid bilayer of the cell membrane in order to enter the bloodstream. Bioavailability is also complicated by the non-aqueous behaviour of some mucosal surface milieus such as the amphipathic behaviour of lung surfactant at the pulmonary mucosal surface.

Hydrophobic bioactive agents in particular suffer from drawbacks in dosage formulation and bioavailability. Dosage formulations are often liquid, with the use of hydrophobic solvent such as oils or ethanol. Frequently, detergents are added to hydrophobic bioactive agent suspensions to enable formation of emulsions. Emulsions can improve bioavailability by placing the bioactive agent in suspension or a discontinuous array of droplets. Bioavailability from emulsion formulations is still limited. Intestinal mobility often moves these preparations past the absorption window in the proximal small bowel before these droplets or suspended particles are reduced in size sufficiently to be absorbed. Moreover, the manufacture and storage of emulsions is problematic due to phase separation and partitioning. A number of hydrophobic bioactive agents such as Cyclosporine A (CyA), Cephalosporins, amphotericins, griseofulvins, and other antifungals and antibiotics, taxols and vitamins would be improved by the formulation of dosage forms with increased bioavailability. The wide variety of bioactive agents includes, but is not limited to, those listed in Table 1.

TABLE 1

| Antiasthma | Antiarrhythmic | Tranquilizers |
|---|---|---|
| metaproterenol | propanolol | chlorpromazine |
| aminophylline | etanolol | benzodiazepine |
| theophylline | verapamil | butyrophenomes |
| terbutaline | captopril | hydroxyzines |
| Tegretol | isosorbide | meprobamate |
| ephedrine | | phenothiazines |
| isoproterenol | | reserpine |
| adrenaline | | thioxanthines |
| norepinephrine | | |
| Cardiac glycosides | Hormones | Steroids |
| digitalis | antidiuretic | prednisone |
| digitoxin | corticosteroids | triamcinolone |
| lanatoside C | testosterone | hydrocortisone |
| digoxin | estrogen | dexamethasone |
| | thyroid | betamethasone |
| | growth | prednisolone |
| | ACTH | |
| | progesterone | |
| | gonadotropin | |
| | mineralocorticoid | |
| Antihypertensives | Antidiabetic | Antihistamines |
| apresoline | Diabenese | pyribenzamine |
| etanolol | insuiin | chlorpheniramine |
| | | diphenhydramine |
| Antiparasitic | Anticancer | Sedatives & Analgesic |
| praziquantel | azathioprine | morphine |
| metronidazole | bleomycin | dilaudid |
| pentamidine | byclophosphamide | codeine |
| | adriamycin | codeine-like synthetics |
| | daunorubicin | Demerol |
| | vincristine | oxymorphone |
| | | Phenobarbital |
| | | barbiturates |
| Antibiotic | Immunotherapies | Vaccines |
| amphotericins | interferon | influenza |
| penicillin | interleukin-2 | respiratory syncytial |
| tetracycline | monoclonal antibodies | virus |
| erythromycin | gammaglobulin | Hemophilus influenza |
| cephalothin | | vaccine |
| imipenem | Antifungal | Antiviral |
| cefofaxime | amphotericin B | acyclovir and derivatives |
| carbenicillin | myconazole | Winthrop-51711 |
| vancomycin | muramyl dipeptide | ribavirin |
| gentamycin | clotrimazole | rimantadine/amantadine |
| tobramycin | Antihypotensives | azidothymidine & |
| piperacillin | dopamine | derivatives |
| moxalactam | dextroamphetamine | adenine arabinoside |
| amoxicillin | | amidine-type protease |
| ampicillin | | inhibitors |
| cefazolin | | Other |
| cefadroxil | | receptor agonists and |
| cefoxitin | | antagonists |
| other aminoglycosides | | |
| other cephalosporins | | |

One of the most frequently used hydrophobic bioactive agents, CyA is virtually insoluble in aqueous solvents and soluble in ethanol or fixed oils. The two most common dosage forms of CyA are administered as an oil formulation that must be formed into a microemulsion prior to absorption. These two formulations, Neoral® and Sandimmune® essentially differ in their bioavailability in that the former forms microemulsions more efficiently and this formulation shows significantly better bioavailability. GB Patent No. 2,257,359A. Neither formulation allows for a dry formulation such as a tablet or powder which would be of considerable benefit with respect to manufacture and storage of the drug.

CyA is of particular importance as it is being used not only as an immunosuppressant in transplant patients, but also as a treatment for asthma, dermatitis and arthritis. EP 577,544; EP 504,760 Tominaga et al. (1995) *Gen. Pharmac.* 26:353–356; and Arima et al. (1994) *Jpn. J Allergol.* 43:1316–1325. Dosage forms for treating asthma, other pulmonary conditions or for by-inhalation administration are most often in the form of aerosols of a fine mist of aqueous droplets. Several dosage forms and devices for by-inhalation delivery of hydrophobic bioactive agents have been described. These include small particle aerosol liposomes, aerosolized ethanol; and ultrasonic nebulizers. EP 267,050; EP 577,544; and Arima et al. (1994). More recently, the pulmonary administration of dry powders, driven by the need to eliminate aerosol propellants, has seen the development of many dry powder inhalers.

A variety of formulations have been provided for administration in aerosolized form to mucosal surfaces, particularly "by-inhalation" (nasopharyngeal and pulmonary). Compositions for by-inhalation pharmaceutical administration generally comprise a liquid formulation of the bioactive agent and a device for delivering the liquid in aerosolized form. U.S. Pat. No. 5,011,678 describes suitable compositions containing a pharmaceutically active substance, a biocompatible amphiphilic steroid and a biocompatible (hydro/fluor) carbon propellant. U.S. Pat. No. 5,006,343 describes suitable compositions containing liposomes, pharmaceutically active substances and an amount of alveolar surfactant protein effective to enhance transport of the liposomes across a pulmonary surface.

One drawback to the use of aerosolized formulations is that maintenance of pharmaceutical agents in aqueous suspensions or solutions can lead to aggregation and loss of activity and bioavailability. The loss of activity can be partially prevented by refrigeration; however, this limits the utility of these formulations. This is particularly true in the case of peptides and hormones. For instance, synthetic gonadotropin releasing hormone analogs, such as the agonist nafarelin or the antagonist ganirelex, are designed for high potency, increased hydrophobicity and membrane binding. The compounds have sufficient hydrophobic character to aggregate in aqueous solution and to form an ordered structure that increases in viscosity with time. Thus, bioavailability in nasal or pulmonary formulations can be prohibitively low.

DISCLOSURE OF THE INVENTION

The invention encompasses methods of making compositions with increased bioavailability for mucosal delivery of bioactive agents. The invention further comprises the compositions obtained thereby. In one embodiment, the compositions contain bioactive agents and hydrophobically-derivatized (substituted) carbohydrates (HDCS) in powder form. In another embodiment, the dosage forms contain bioactive agents, HDCs and surfactants in powder form. The compositions form solid solutions, suspensions or emulsions of bioactive agents, with or without modifiers and/or other additives, in an HDC glass.

The invention also encompasses methods of making compositions of suspensions of bioactive agents in aqueous solvents and the compositions obtained thereby. The methods include obtaining the compositions described above and dispersing the glass in an aqueous solvent suitable for administration. The compositions obtained thereby are also suitable for use as a solid dose form.

The compositions described herein are also suitable for delivery of pharmaceutical agents, particularly hydrophobic agents, as well as other biologically active agents such as flavourings, dyes, pesticides and cosmetics.

BEST MODE FOR CARRYING OUT THE INVENTION

Figure 1:
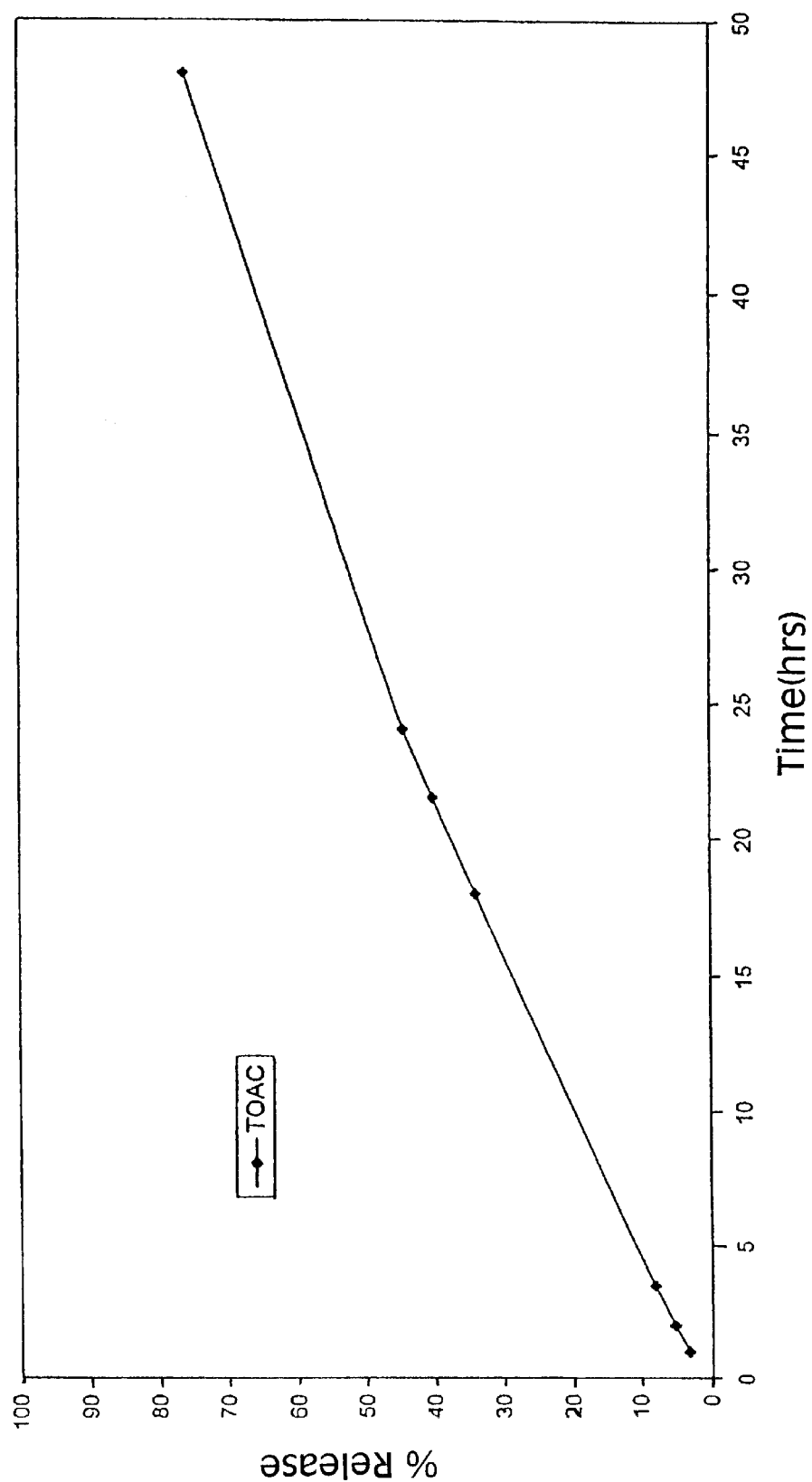
FIG. 1 is a graph depicting the percent release of a model hydrophobic bioactive agent, the dye disperse red 1 (DR1) incorporated in a single HDC vehicle, into a detergent containing medium [3% (w/v) sodium dodecyl sulphate in 0.9% saline solution] to mimic a surface active mucosal milieu. The HDC illustrated is trehalose octaacetate incorporating 1.4% (w/w) DR1. The identical formulation showed no release of DRI into a saline solution over a 5 day test period.

The compositions of the present invention are readily formulated into glasses suitable as dosage forms with increased bioavailability for mucosal delivery of bioactive agents. It has now been found that the dosage forms described herein tailored for delivery to different mucosal surfaces allow for increased bioavailability of bioactive agents, particularly hydrophobic drugs. For instance, as shown below, a solution mimicking lung surfactant allows for release of bioactive agent from the compositions described herein which lack a surface active agent. This is in contrast to the lack of release of these same formulations in saline. Alternatively, to improve release of bioactive agents from the dosage forms described herein for delivery to mucosal surfaces such as gastrointestinal and ocular, the addition of surfactants to the compositions provides increased bioavailability. This is graphically depicted in an animal model system where CyA (Cyclosporine A) delivery from a dosage form containing surfactant is improved over a control. These results are shown in the Examples below.

The invention encompasses methods of making glasses for use in making dosage forms providing increased bioavailability of bioactive agents through mucosal delivery. The glasses contain both a bioactive agent and a surface active agent in solid solution, suspension or emulsion phase of HDCs. Hydrophilic surfactants, i.e. those with a high hydrophile-lipophile balance (HLB), readily form a continuous phase with these HDC glasses which are stable during processing and storage. It has now been found that these glasses release more bioactive agent in aqueous buffers than matrices not containing surfactants. These "solid solutions" are highly stable; they show no sign of phase separation for up to 4 weeks at room temperature and the hydrophobic bioactive agent incorporated therein can be quantitatively extracted by organic solvent extraction and shows no evidence of degradation of analysis by HPLC. The glass obtained can be in the vitreous or crystalline form or mixtures thereof. The glass can also be an amorphous matrix. As used herein, "glass", glasses" or "glassy" refers to all of these embodiments.

The invention thus encompasses compositions of bioactive agents and HDCs in powder form. The invention further encompasses compositions of bioactive agents, HDCs and surface active agents in powder form. These powders can be made either from the melt of the HDC incorporating the bioactive agent or by evaporation from non-aqueous solutions of the HDC and the bioactive agent. The compositions obtained from the melt can be processed to a powder by any method known in the art such as milling. The powders are suitable for use as solid dose forms or can be further processed into tablets or other dosage forms.

The invention further encompasses compositions of hydrophobic bioactive agents, HDCs and surface active agents. The compositions form solid suspensions, solutions or emulsions. The compositions obtained thereby are suitable for use as dosage forms or can be processed into other forms such as powders.

The invention also encompasses methods of making compositions of stable formulations of hydrophobic, bioactive agents in aqueous solution and the compositions obtained thereby. The methods include obtaining the glasses described above and dispersing the solid phase in an aqueous solvent. The compositions obtained thereby are also suitable for use as a pharmaceutical dosage form.

There are a wide variety of bioactive agents suitable for use in the present invention. A number of these are illustrated in Table 1. The various classes of bioactive agents include, but are not limited to, antiinflammatory bioactive agents, analgesics, antiarthritic bioactive agents, antispasmodics, antidepressants, antipsychotics, tranquilizers, antianxiety bioactive agents, narcotic antagonists, antiparkinsonism agents, cholinergic agonists, chemotherapeutic bioactive agents, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular bioactive agents, opioids, and the like. Any suitable bioactive agent can be used. The invention is particularly suited for use with hydrophobic bioactive agents. Suitable concentrations and dosage levels are known in the art and are described for instance in The Physician's Desk Reference.

HDCs form a group of non-toxic carbohydrate derivatives. HDCs readily form glasses either from a quenched melt or from an evaporated organic solvent. The HDCs can also be processed by the methods known in the art and described for other carbohydrate dosage forms.

As used herein, HDC refers to a wide variety of hydrophobically derivatized carbohydrates where at least one hydroxyl group is substituted with a hydrophobic moiety including, but not limited to, esters and ethers. Numerous examples of suitable HDCs and their syntheses are described in Developments in Food Carbohydrate—2 ed. C. K. Lee, Applied Science Publishers, London (1980); and PCT publication No. 96/03978. Other syntheses are described for instance, in Akoh et al. (1987) *J. Food Sci.* 52:1570; Khan et al. (1933) *Tetra. Letts* 34:7767; Khan (1984) *Pure & Appl. Chem.* 56:833–844; and Khan et al. (1990) *Carb. Res.* 198:275–283. Specific examples of HDCs include, but are not limited to, sorbitol hexaacetate (SHAC), α-glucose pentaacetate (α-GPAC), β-glucose pentaacetate (β-GPAC), 1-O-Octyl-β-D-glucose tetraacetate (OGTA), trehalose octaacetate (TOAC), trehalose octapropionate (TOP), trehalose octa-3,3,dimethylbutyrate (TO33DMB), trehalose diisobutyrate hexaacetate, trehalose octaisobutyrate, lactose octaacetate, sucrose octaacetate (SOAC), cellobiose octaacetate (COAC), raffinose undecaacetate (RUDA), sucrose octapropanoate, cellobiose octapropanoate, raffinose undecapropanoate, tetra-O-methyl trehalose, trehalose octapivalate, trehalose hexaacetate dipivalate and di-O-methyl-hexa-O-actyl sucrose and mixtures thereof. An example of a suitable HDC where the carbohydrate is trehalose is:

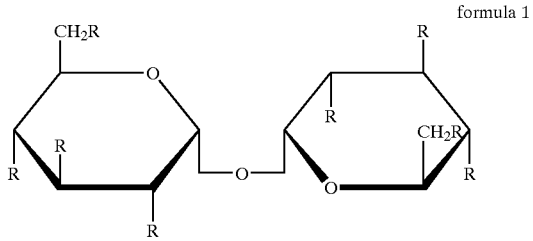

formula 1

In formula 1, R represents a hydroxyl group, or less hydrophilic derivative thereof, such as an ester or ether or any functional modifications thereof where at least one R is not hydroxyl but a hydrophobic derivative. Suitable functional modifications include, but are not limited to, replacing the oxygen atom with a heteroatom, such as N or S. The degree of substitution can also vary, and can be a mixture of distinct derivatives and/or linkages. Full substitution of the hydroxyl groups need not occur and provides an option to alter physical properties (such as solubility) of the vehicle. R can be of any chain length from $C_2$ upwards and can be straight, branched, cyclic or modified and mixtures thereof. While formula 1 depicts the disaccharide trehalose, any of the carbohydrates discussed herein can be the carbohydrate backbone and the position of the glycosidic linkage and saccharide chain length can vary. Typically, the practical range in terms of cost and efficiency of synthesis is a pentasaccharide; however, the invention is not limited to saccharides of any particular type, glycosidic linkage or chain length. Various other aspects of the HDCs are not limiting. For instance, the component saccharides of each HDC can also be varied, the position and nature of the glycosidic bonding between the saccharides can be altered and the type of substitution can vary within an HDC.

The ability to modify the properties of HDCs by slight alterations in chemical structure renders them uniquely suited to use as delivery vehicles for bioactive agents, particularly compared to polymeric systems which often depend on regions of crystallinity to vary their properties, particularly bioerosion. The HDC vehicles can be tailored to have precise properties such as well-defined release rates of bioactive agents. Such tailoring can be by varying the modifications of a particular carbohydrate or by combining a variety of different HDCs.

Pure single HDC glasses have been found to be stable at ambient temperatures and up to at least 60% humidity and even mixtures of HDC glasses incorporating certain bioactive agents are stable at ambient temperatures and up to at least 95% humidity. Incorporation of even 10% (w/v) of extremely hygroscopic bioactive agents, such as the synthetic corticosteroids, yields HDC glasses that are stable when exposed to relative humidities of up to 95% at room temperature for over a month, yet immediately release the bioactive agents within 5–10 minutes upon addition to aqueous solvents.

Adding other HDCs at these same levels to the formulations also produced mixed HDC glasses that were equally resistant to devitrification at 95% relative humidity. The ability to tailor the dissolution rates of composite HDC glasses makes them particularly useful as controlled release delivery vehicles for mucosal delivery.

The HDC glasses can be formed either from evaporation of the solvent or by quenching of the HDC melt. Because of the low softening points of certain HDC glasses, thermally labile bioactive agents such as bioactive agents and biological molecules can be incorporated into the HDC melt during processing without decomposition. Surprisingly, these bioactive agents have demonstrated zero order release kinetics when the forming compositions erode in aqueous solution. When the composition is in vitreous form, release follows the process of surface devitrification. The HDC vehicles can be easily modeled into any shape or form, such as those described herein. Such modeling can be by extrusion, molding etc. by any method known in the art. The HDCs are suitable for use as delivery vehicles as they are non-toxic and inert to any solutes which can be incorporated therein.

The vitreous forms of the compositions undergo heterogeneous surface erosion when placed in an aqueous environment, making the compositions particularly suited to mucosal delivery. While not being bound by any one theory, one possible mechanism for degradation of the compositions begins with an initial surface devitrification as supersaturation occurs at the interface, followed by subsequent erosion and/or dissolution of the surface layers at a slower rate. The compositions can be modified by careful selection of components to give the desired devitrification rates and hence the required release rates of the bioactive agent as the devitrified layer provides no barrier to the release of the bioactive agent.

We have now also found that the incorporation and release of hydrophobic bioactive agents from the compositions can be enhanced by the incorporation of surface active agents during the formation of the compositions. Suitable surfactants are those with a high HLB, i.e., those that are hydrophilic with a HLB of at least about 3. Preferably, the surfactants are dry at room temperature. Suitable surfactants include, but are not limited to, glyceryl monostearate, sorbitan monolaurate, polyoxyethylene-4-lauryl ether, polyethylene glycol 400 monostearate, polyoxyethylene-4-sorbitan monolaurate, polyoxyethylene-20-sorbitan monopalmitate, polyoxyethylene-40-stearate, sodium oleate and sodium lauryl sulfate. Suitable surfactants also include lung surfactants both naturally derived and synthetically manufactured. A suitable artificial lung surfactant is described for instance in Bangham et al. (1979) *Biochim. Biophys. Acta* 573:552–556. Suitable concentrations of surfactants can be empirically derived as described in Example 4.

In one embodiment, the dosage forms are in the form of a powder. These are particularly suitable for use in by-inhalation delivery systems. Preferably the powders are of a particle size of about 0.1 to 10 microns. More preferably, the particle size is about 0.5 to 5 microns. Most preferably, particle size is about 1 to 4 microns. In particular for pulmonary administration, the preferred particle size is about 2.5–3 microns. For use in oral administration, the particles can be of any size.

The compositions can be formulated into a wide variety of dosage forms based on further processing of the powders. These include, but are not limited to, suspensions in liquids, gels or creams, filled capsules, pessaries, gel/polymer matrices and tablets.

For instance, the powders can be suspended in juices or other palatable liquids for oral administration. The powders can be suspended in physiologically acceptable solutions for ocular administration. Dosage forms suitable for ocular administration include, but are not limited to, microsphere and macrosphere formulations and saline drops, creams and ointments containing these. A wide variety of physiologically acceptable gels, creams and liquids are known in the art. The compositions can contain other ingredients conventional in pharmaceutical compositions including, but not limited to, flavorants, perfumes, hormones such as estrogen, Vitamins such as A, C or E, alpha-hydroxy or alpha-keto acids such as pyruvic, lactic or glycolic acids, lanolin, vaseline, aloe vera, methyl or propyl paraben, pigments and the like.

In one method of making the compositions, the bioactive agent and HDC(s) (and, optionally, surfactant) are mixed, melted to form a homogeneous mix that is then rapidly quenched to a glass incorporating the bioactive agent and the surfactant (if added). The HDC melts are excellent solvents for many organic molecules. This makes them particularly suitable for use in delivery of bioactive materials otherwise difficult to formulate. More than 20% weight percent of organic molecules can be incorporated into the compositions. Notably, HDCs are inert and show no reactivity to their solutes or bioactive agents incorporated therein.

In another method of making the compositions, the HDCs and bioactive agents (and, optionally, surfactants) are dissolved in at least one solvent therefor and the glass incorporating the bioactive agent (and surfactant) is formed by evaporation of the solvent. Suitable solvents include, but are not limited to, dichloromethane, chloroform, dimethylsulfoxide, dimethyformamide, acetone, ethanol, propanol and the higher alcohols. The nature of the solvent is immaterial as it is removed in the formation of the delivery system. On evaporating the solvent, the HDCs concentrate to form a glass incorporating the bioactive agent with properties similar to the glass formed by quenching from the melt.

Other methods of making the compositions include, but are not limited to, spray drying, freeze drying, air drying, vacuum drying, fluidized-bed drying, milling, co-precipitation and super-critical fluid evaporation. In these methods, the HDC, bioactive agent and any other components are first dissolved or suspended in suitable solvents. In the case of milling, glasses formed from the components, either by solvent evaporation or quenching of the melt, are milled in the dried form and processed by any method known in the art. In the case of co-precipitation, the components are mixed in organic conditions and processed as described above.

In the case of spray drying, the components are mixed under suitable solvent conditions and dried using precision nozzles to produce extremely uniform droplets in a drying chamber. Suitable spray drying machines include, but are not limited to, Buchi, NIRO, APV and Lab-plant spray dryers used according to the manufacturer's instructions.

The following examples are meant to illustrate but not limit the invention.

EXAMPLE 1

Release of Model Bioactive Agent from Single HDC Solid Dose Form into Surface Active Mucosal Milieu Mimic The dye disperse red (DR1) was used as a model bioactive agent to assess their bioavailability when incorporated in a composition comprising a single HDC in an in vitro model with the use of a detergent containing medium [3% (w/v) sodium dodecyl sulphate in 0.9% saline solution] to mimic a surface active mucosal milieu. The HDC illustrated is trehalose octaacetate incorporating 1.4% (w/w) DR1. The dye was incorporated in the composition by dissolving the dye in a melt of the HDC and quenching the melt in a stainless steel mould (1.3 cm diameter) to form the solid dose form. The release of dye from the solid dose form into the mucosal milieu mimic was assessed in USP (vol. 23) type 2 dissolution studies, using a Distek (Model 2100) dissolution system and the dye released was quantitated spectrophotometrically at 502 nm using a Hewlett-Packard (Model 8453) diode array spectrophotometer. The results obtained are illustrated in FIG. 1. The identical solid dose form showed no release of DR1 into a saline solution over a 5 day test period.

EXAMPLE 2

Figure 2:
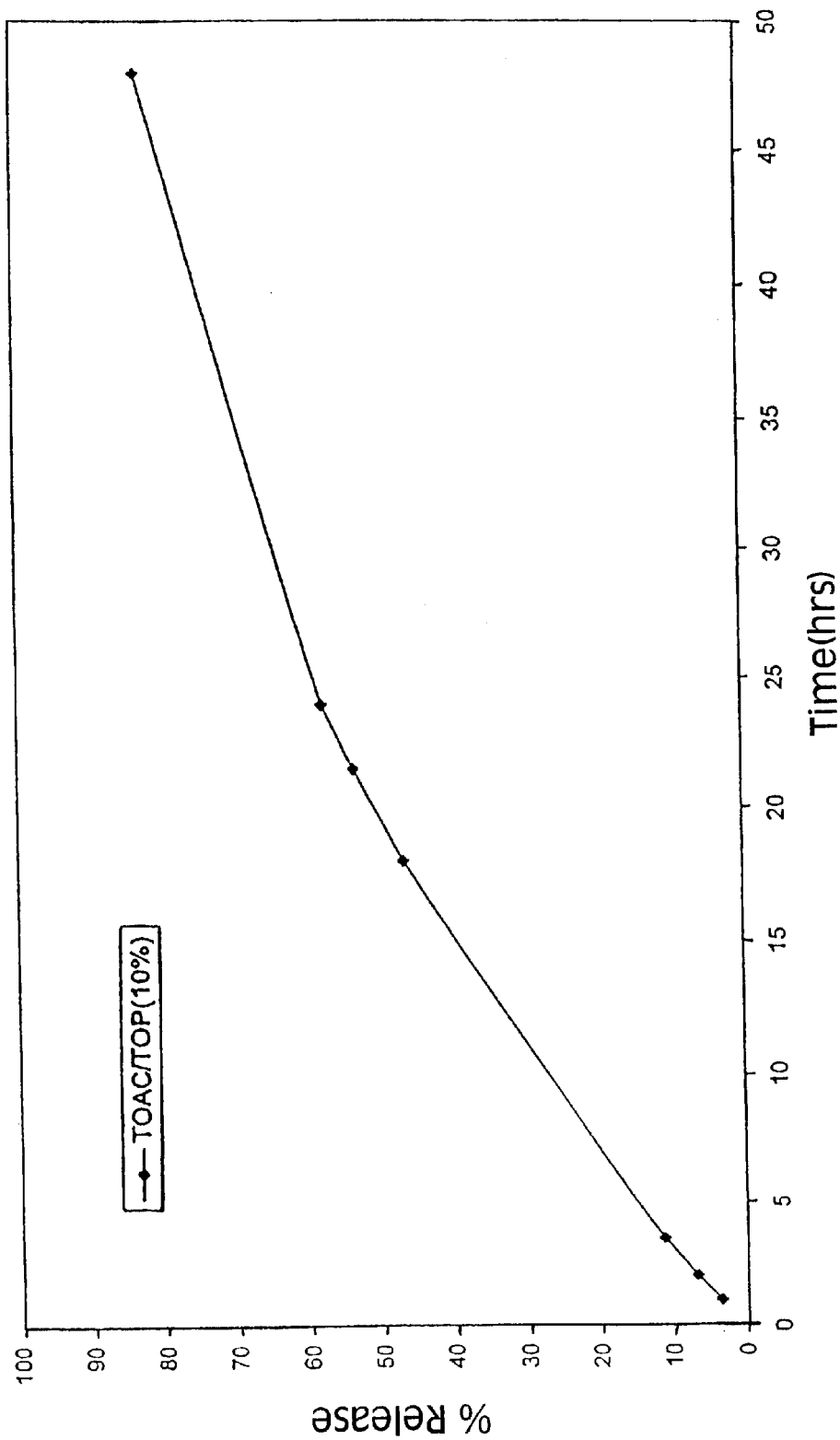
FIG. 2 is a graph depicting the percent release of DR1 incorporated in a mixed HDC vehicle, into a detergent containing medium [3% (w/v) sodium dodecyl sulphate in 0.9% saline solution] to mimic a surface active mucosal milieu. The HDC mix illustrated is trehalose octaacetate/ trehalose octapropionate (ratio 10:1) incorporating 1.4% (w/w) DR1. The identical formulation showed no release of DR1 into a saline solution over a 5 day test period.

Release of Model Bioactive Agent from Mixed HDCs Solid Dosage Form into Surface Active Mucosal Milieu Mimic The bioavailability of bioactive agents incorporated in solid dose forms of mixed HDCs was assayed in an in vitro model as described in Example 1. The composition illustrated is trehalose octaacetate/trehalose octaproprionate (ratio 1:10) incorporating 1.4% (w/w) DR1. The release of DR1 from the solid dose form into a detergent containing medium [3% (w/v) sodium dodecyl sulphate in 0.9% saline solution] to mimic a surface active mucosal milieu was determined as described in Example 1. The results obtained are shown in FIG. 2 and again the identical solid dose form showed no release of DR1 into a saline solution over the 5 day test period.

EXAMPLE 3

Figure 3:
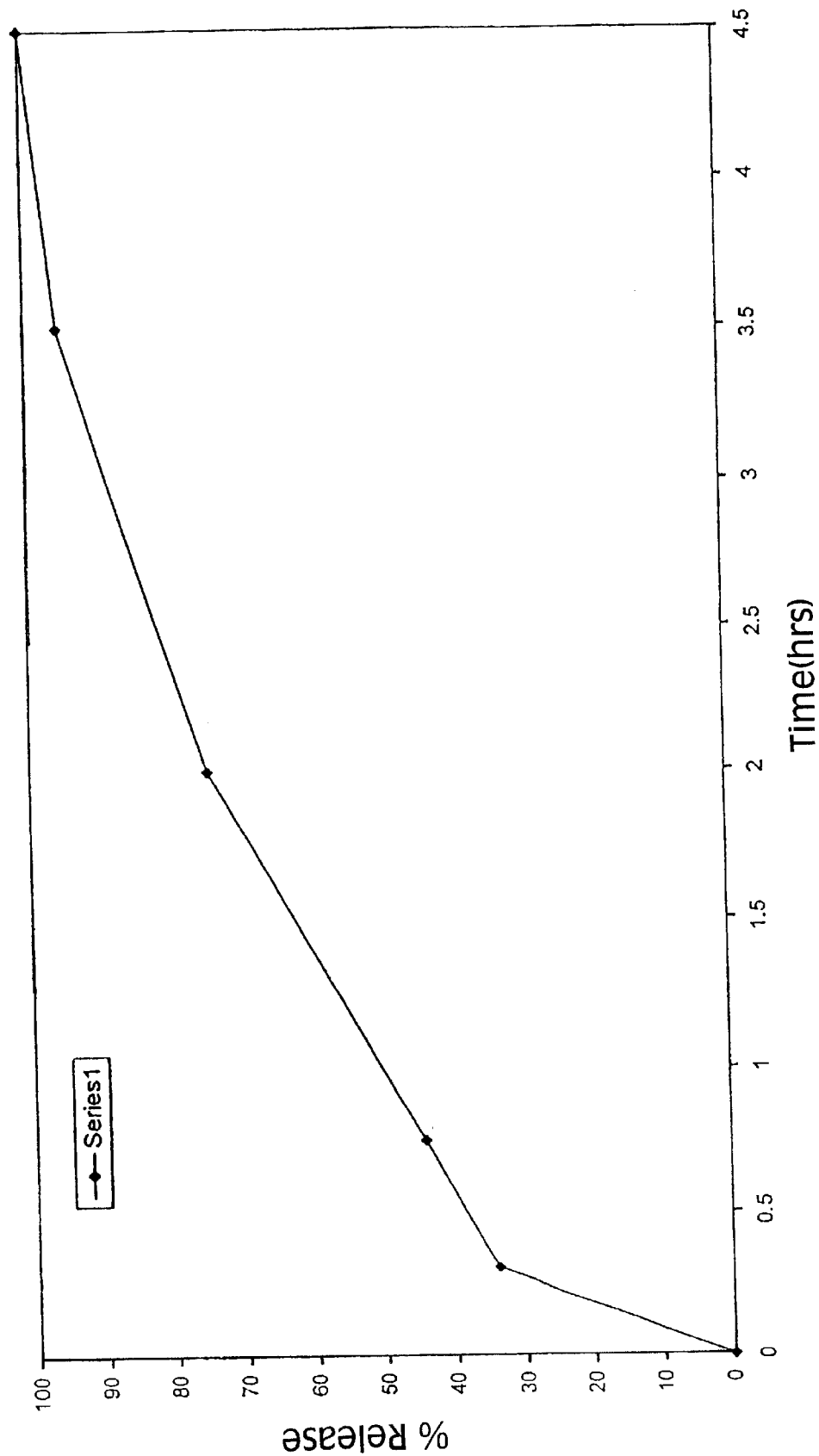
FIG. 3 is a graph depicting the percent release of a model hydrophobic bioactive agent melatonin, incorporated in a solid dose form, into a detergent containing medium [5% (w/v) Tween 80 in 0.9% saline solution] to mimic a surface active mucosal milieu. The HDC illustrated is trehalose octa-3,3 dimethylbutyrate incorporating 4% (w/w) melatonin. The identical formulation showed no release of melatonin into a saline solution over a 5 day test period.

Release of Hydrophobic Pharmaceutical Bioactive Agent from HDC Solid Dose Form into Surface Active Mucosal Milieu Mimic The bioavailability of a hydrophobic pharmaceutical bioactive agent, melatonin, incorporated in a solid dose form was assayed in an in vitro model as described in Example 1. The solid dose form illustrated is trehalose octa-3,3 dimethylbutyrate incorporating 4% (w/w) melatonin. The detergent containing medium used to mimic the surface active mucosal milieu was 5% (w/v) Tween 80 in 0.9% saline solution. The results obtained are illustrated in FIG. 3 and again studies on the release of melatonin from an identical formulation into a saline solution with no surface active agent showed no release of melatonin the 5 day test period.

EXAMPLE 4

Figure 4:
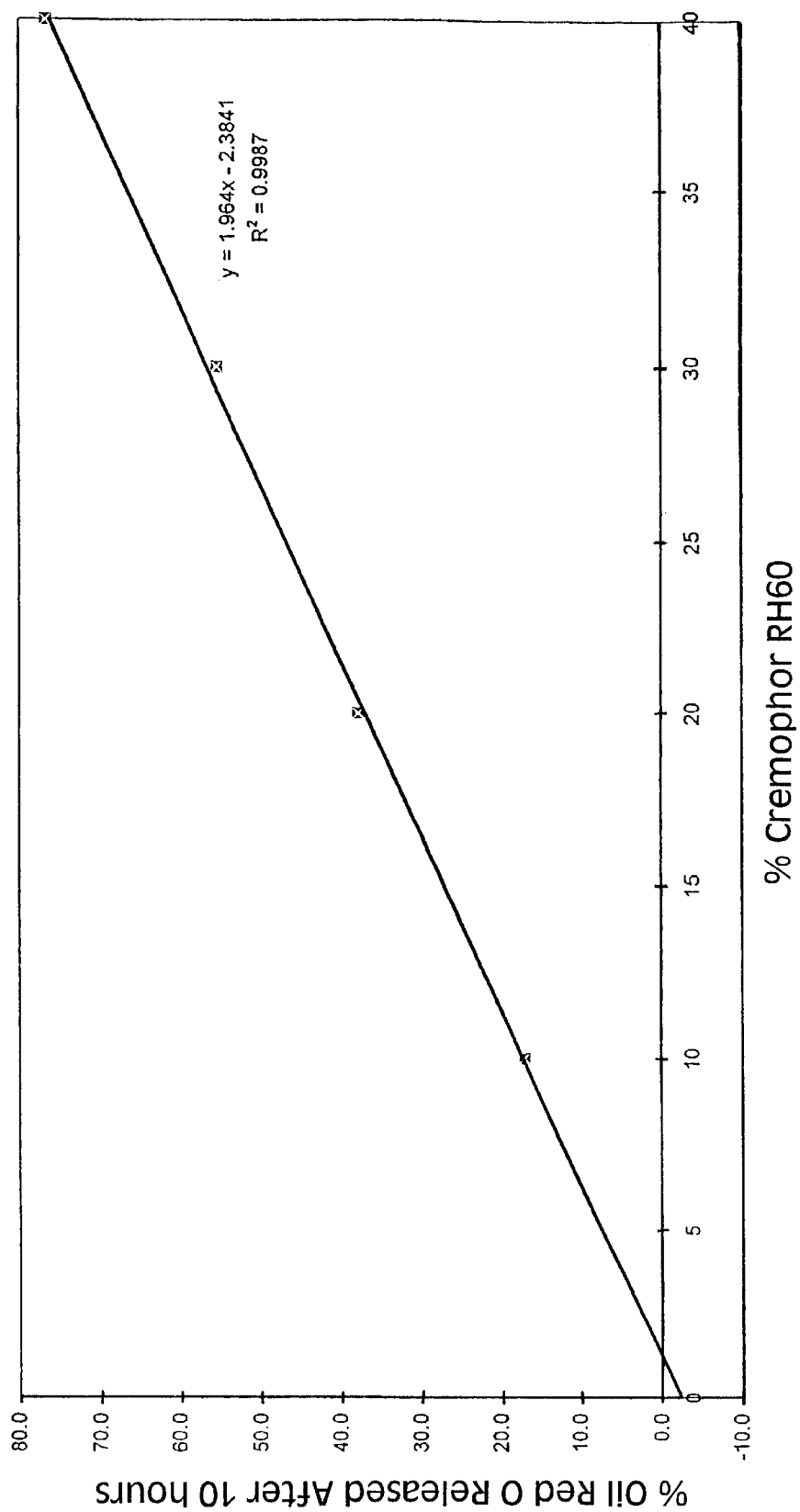
FIG. 4 is a graph depicting the relationship between the mean release of a model hydrophobic molecule Oil Red O (ORO) at 10 hours from solid dose forms containing varying concentrations of surfactant. The HDC used is trehalose octaacetate (TOAC) and the surfactant is Cremophor RH60.

Effect of Incorporated Surface Active Agent on Release of Model Hydrophobic Bioactive Agent from HDC Solid Dose Form The effect of incorporated surfactant on release of hydrophobic model bioactive agent from a solid dose form was tested using Oil Red O as a model hydrophobic bioactive agent incorporated in a solid dose form comprising trehalose octaacetate and a surfactant. Basically, 1% (w/w) of the hydrophobic dye oil red O (ORO) was mixed with 10–40% (w/w) surfactant (Cremophor RH60) and trehalose octaacetate and melted in a furnace at about 200° C. The melt was swirled until all the ORO visibly dissolved and the melt was quenched rapidly in 10 mm brass rings on a metal plate and allow to set before removing the resulting glass disc solid dose form. The release of dye from the solid dose form was assessed using an in vitro USP (volume 23) type 2 dissolution test in 0.1M HCl as the dissolution medium. The USP 2 dissolution apparatus containing 900 ml 0.1M HCl at 37° C. stirred at 100 rpm and samples of approximately 5 ml taken hourly and assayed by UV spectroscopy at 523 nm in 10 mm cell against a 0.1M HCl reference cell. The assay data were corrected for ongoing media loss during the test. The results obtained are summarized in FIG. 4. A linear correlation between the amount of ORO detected in solution after 10 hours and the amount of surfactant in the formulation (FIG. 4). Similar results were also obtained with other surfactants such as other commercial hydrogenated castor oils and sorbitan and pluronic surfactants.

EXAMPLE 5

Bioavailability Study of Oral Delivery of a Peptide

Three groups of six rats were dosed with the peptide macrolide Cyclosporine A (CyA) presented as two different solid dose forms QA and QB and compared with the best current commercial formulation. Both formulation QA and QB were made by solvent evaporation of a 10% solution of CyA in trehalose octaacetate (HDC) dissolved in $CH_2Cl_2$, either with (QB) or without (QA) added Lutrol F127 (surfactant, ICI). The dry compositions were milled and the resulting powder dispersed in carboxymethylcellulose suspending medium (3 mg CyA per ml of medium) and a dose of 10 mg/kg administered by oral gavage. The commercial preparation was diluted 1:14 with carboxymethylcellulose suspending medium and again administered by oral gavage to a control group of six rats; the higher dosage of 22 mg/kg for the commercial formulations is corrected for in the results in FIG. 5. Blood samples were taken by cardiac puncture at intervals over 24 hours and assayed using a commercial immunoassay.

Figure 5:
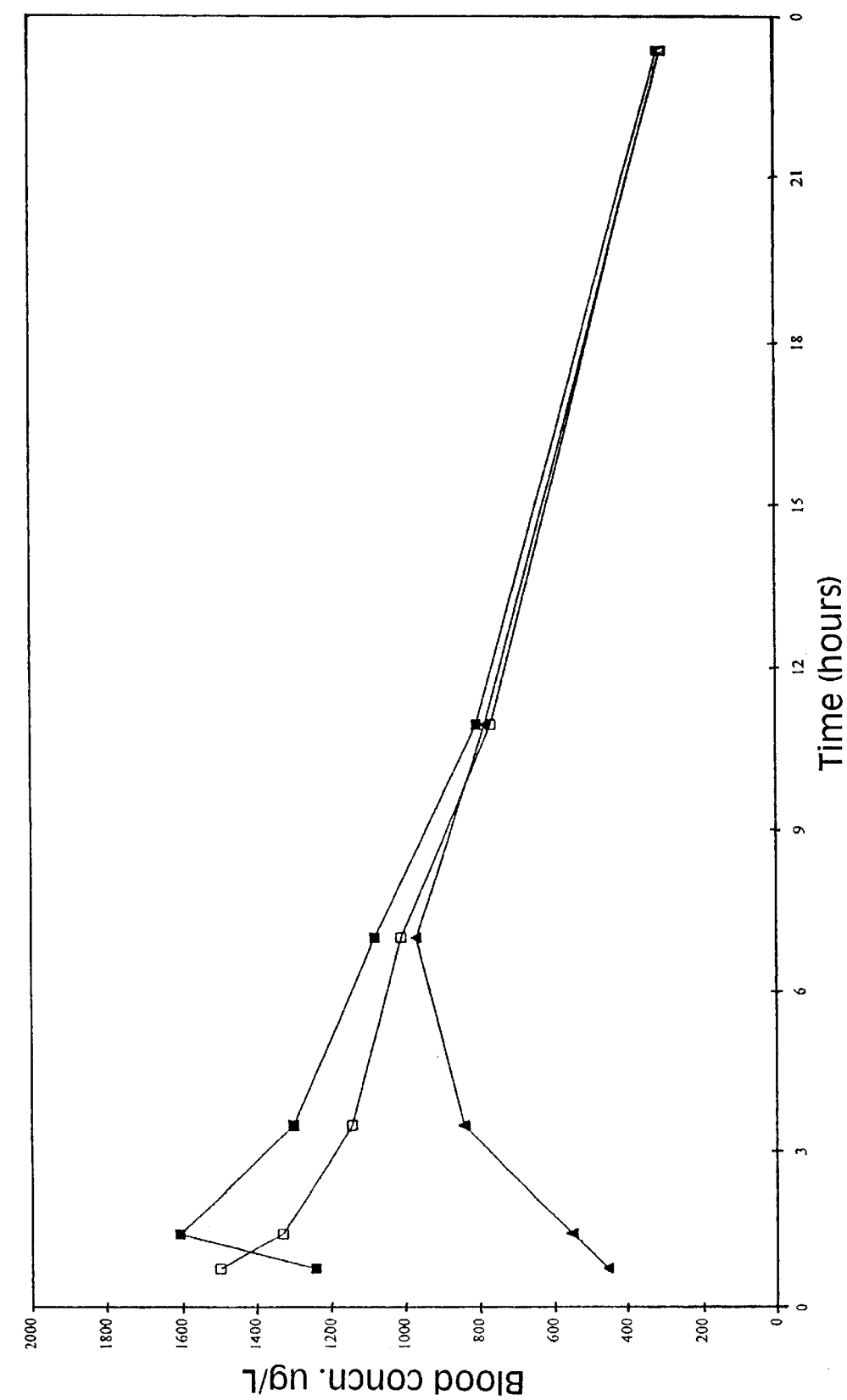
FIG. 5 is a graph depicting the bio-availability of CyA in the rat. The open squares represent the blood levels of CyA detected on administration of the QA test formulation (CyA plus surfactant in HDC) at a 10 mg/kg dose. The closed triangles represent the blood levels of CyA detected on administration of the QB test formulation (CyA in HDC alone) administered at a 10 mg/kg dose. The closed squares represent a commercial oil formulation of CyA administered at a 20 mg/kg dose with the data for blood levels corrected to represent an equivalent 10 mg/kg dose.

The results obtained are summarized in FIG. 5. Both formulations QA and QB showed significantly improved bioavailability over results on the administration of CyA alone reported in the literature which show no detectable levels of drug detectable in the blood up to 2 hours after administration. The QA formulation containing surfactant showed even better bioavailability than the QB formulation with a profile essentially similar ($AUC_{1-24}$ and Cmax) to the best commercial formulation (96% comparative bioavailability). (FIG. 5).

EXAMPLE 6

Bioavailability Study of Oral Delivery of Organic Molecule

Figure 6:
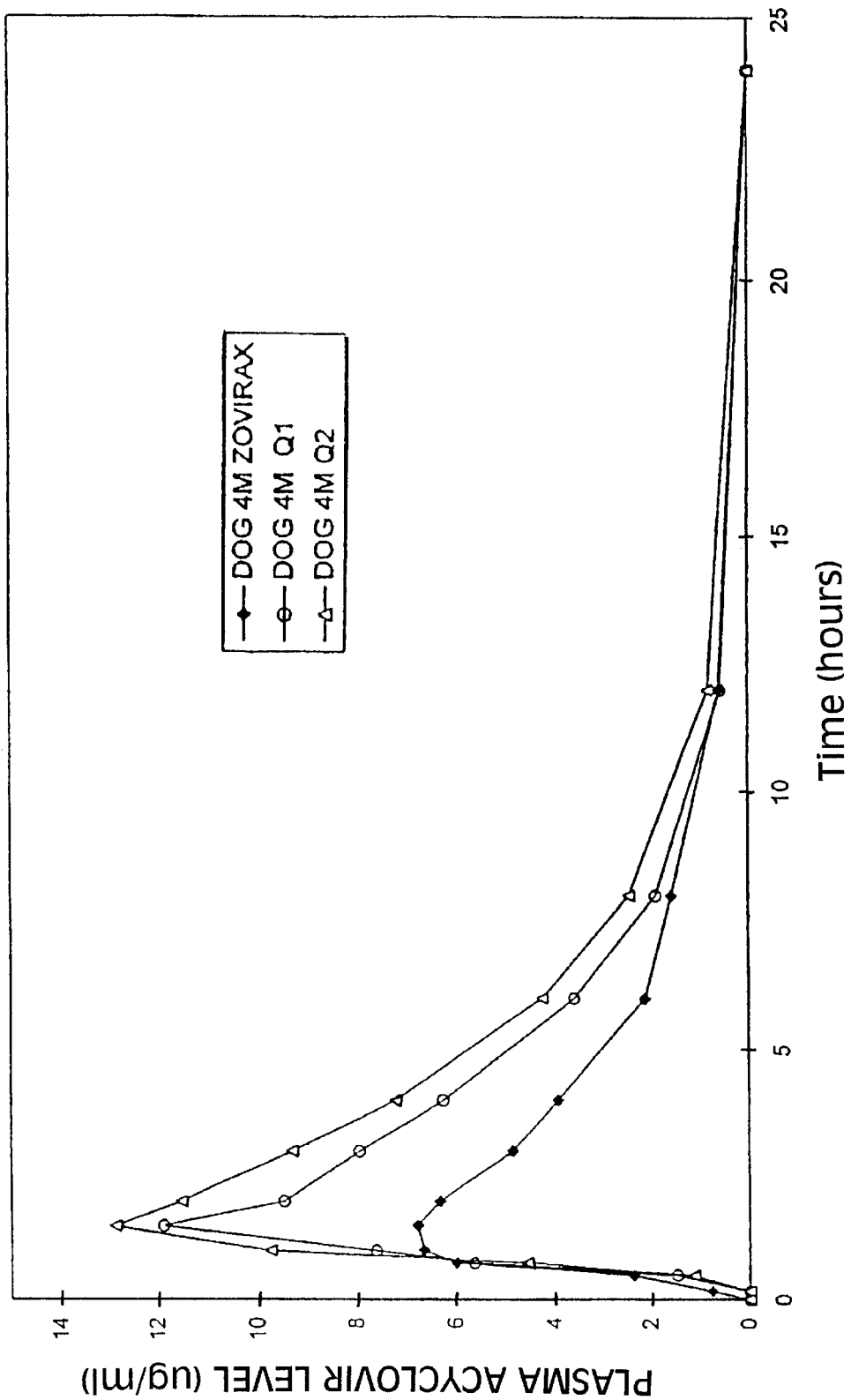
FIG. 6 is a graph depicting the bio-availability of orally dosed with solid dose forms of acyclovir in the dog. The open circles represent the blood levels of acyclovir detected on administration of the Q1 test formulation (vehicle of trehalose octaacetate and surfactant containing 5% acyclovir) at a 10 mg/kg dose. The open triangles represent the blood levels of acyclovir detected on administration of the Q2 test formulation (solid dose vehicle of trehalose octaacetate and surfactant containing 25% acyclovir) at a 10 mg/kg dose. The closed diamonds represent a commercial formulation of acyclovir administered at a 10 mg/kg dose.

Dogs were dosed via the oral route with acyclovir presented as two different novel formulations Q1 and Q2 and compared with the best current commercial formulation (Zovirax). Both formulation Q1 and Q2 were made by solvent removal, by lyophilization of an organic solution of acyclovir and trehalose octaacetate dissolved in dimethylsulphoxide (DMSO), with added Lutrol F127 (surfactant, ICI). The dry solid formulations were milled and orally dosed in gelatin capsules at a nominal dose of 200 mg acyclovir. Blood samples taken periodically and assayed chromatographically for acyclovir using a validated high performance liquid chromatographic analysis. The results of the blood levels of acyclovir obtained are shown in FIG. 6. Both formulations Q1 and Q2 showed significantly improved bioavailability over the commercial preparation administered as a control (FIG. 6).

EXAMPLE 7

Formulation and Oral Delivery of a Protein

Figure 7:
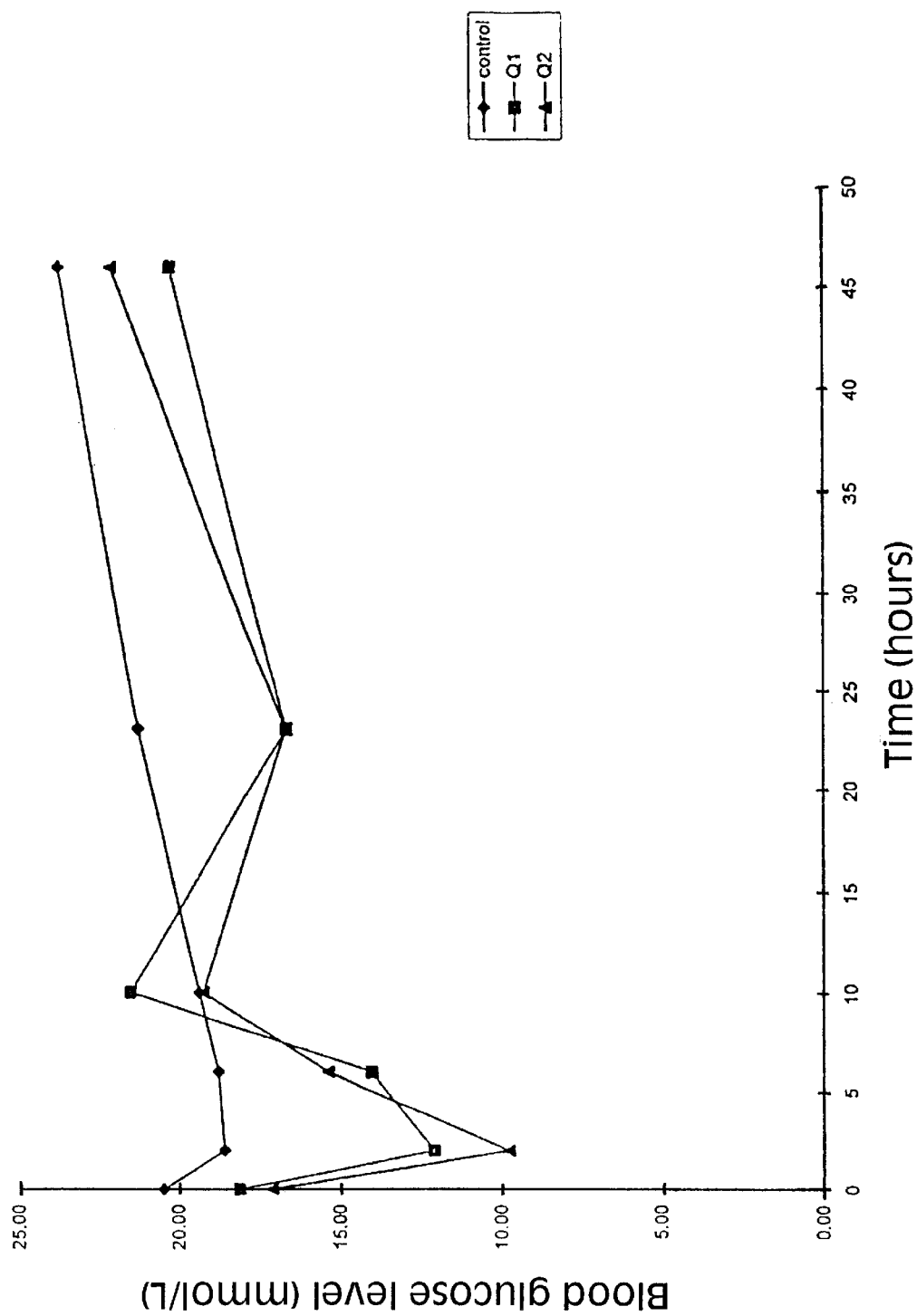
FIG. 7 is a graph depicting the bio-availability of orally dosed with solid dose forms of insulin in the rat. The closed squares represent the blood levels of glucose detected on administration of the Q1 insulin formulation (vehicle of trehalose octaacetate containing 10% insulin). The closed triangles represent the blood levels of glucose detected on administration of the Q2 insulin formulation (vehicle of trehalose octaacetate and surface active agent (10% Epikuron 200:10% oleic acid mixture) containing 10% insulin). The closed diamonds represents the blood levels of glucose detected on administration of a commercial formulation of 10% insulin.

The bioactive polypeptide insulin was formulated (10% loading) in trehalose octaacetate either with or without surface active agent (2.5% sodium taurocholate, 40% Lutrol or a 10% Epikuron 200:10% oleic acid mixture) by solvent evaporation, by lyophilization of a solution of insulin and HDC in DMSO. The Tg of the composition obtained in (Q2) was measured by differential scanning calorimetry (DSC) at 56.6° C. Incorporation of surfactant in the glass showed no effect on the Tg of the formulated delivery vehicle (Tg of trehalose octaacetate formulation with 10% Epikuron 200:10% oleic acid mixture (Q1) was 56.3° C.). Oral administration of 100 i.u. of the formulated insulin by gavage to rats showed a reduction in blood glucose levels showing adsorption of the orally administered insulin from the solid dose forms with or without incorporated surfactant whereas the control formulation showed no effect on blood sugar levels (FIG. 7).

EXAMPLE 8

Bioavailability Study of Pulmonary Delivery of an Organic Molecule in vivo

Figure 8:
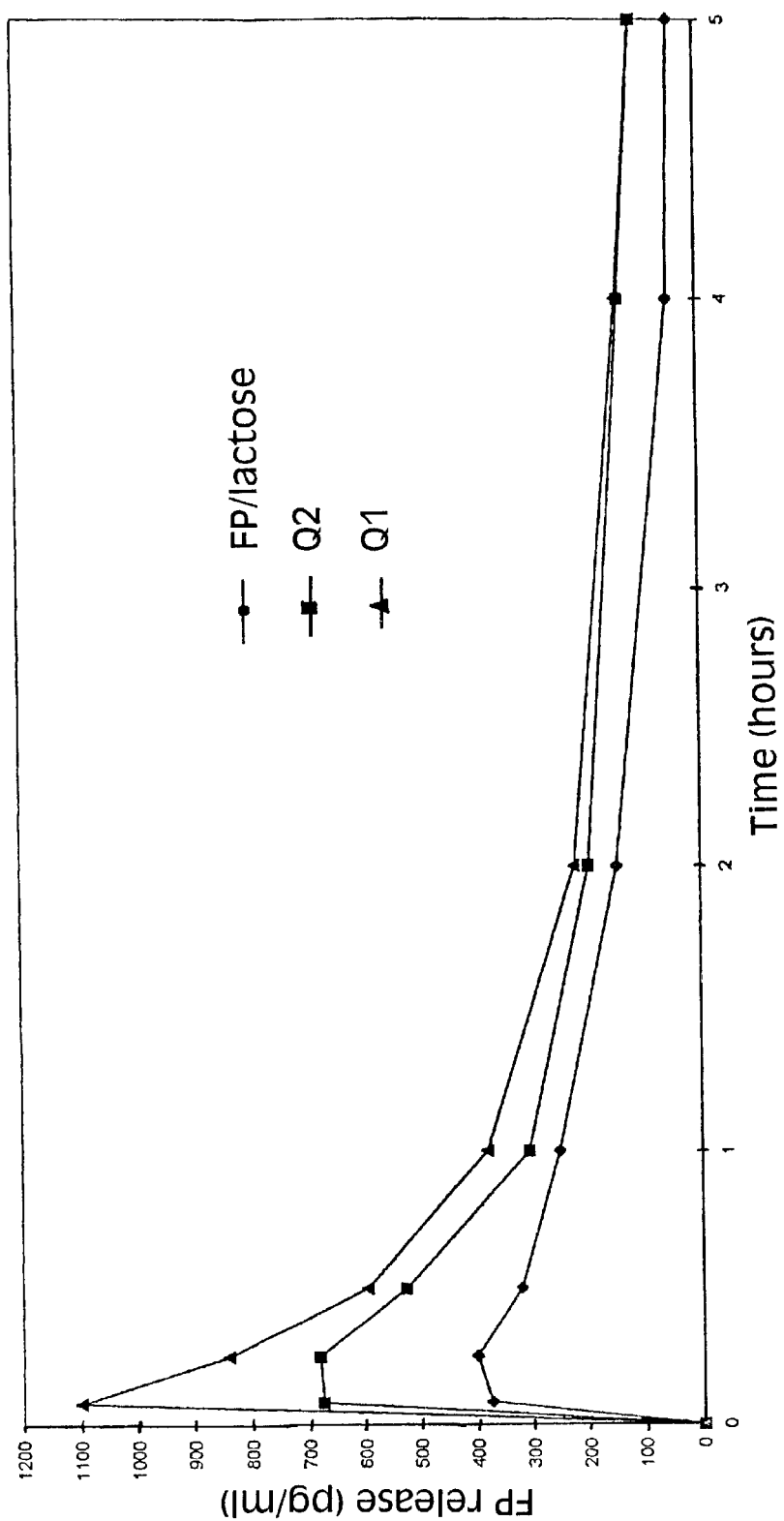
FIG. 8 is a graph depicting the bio-availability of pulmonary dosage of solid dose forms of fluticasone propionate (FP) in the pig. The closed triangles represent the plasma levels of fluticasone propionate detected on the pulmonary administration of the Q1 test formulation (vehicle of trehalose octaacetate containing 5% bioactive agent). The closed squares represent the plasma levels of fluticasone propionate detected on the pulmonary administration of the Q2 test formulation (vehicle of mixed HDCs trehalose octaacetate/ octaisobutyrate (75:25 ratio) containing 5% bioactive agent). The closed diamonds represent the plasma levels of fluticasone propionate detected on the pulmonary administration of a commercial formulation of 5% fluticasone in lactose.

The corticosteroid fluticasone was formulated as a solid dose form in trehalose octaacetate or trehalose octaisobutyrate either as single HDCs or as a mixture of HDCs (90:10 or 75:25 ratios) by quenching from the melt. The HDCs were melted at 150–170° C. and the corticosteroid was dissolved in the melt at 120–140° C. followed by quenching of the melt on a cooled brass plate. The glass obtained was then milled to give a fine powder of average particle size of 5 $\mu$m (±2 $\mu$m) which was administered as a dry powder solid dose form to the lungs of dogs and pigs. Adsorption of fluticasone was analyzed by chromatographic assay for corticosteroid in the blood of the animals at suitable time intervals. In both dogs and pigs the solid dose forms showed enhanced pulmonary bioavailability compared to controls of corticosteroid administered in conventional lactose formulations. The results obtained for pulmonary delivery of corticosteroid in pigs is shown in FIG. 8, with Cmax values of 1103 and 686 and Tmax values of 0.08 and 0.25 respectively for the trehalose octaacetate/octaisobutyrate (75:25) mixed HDC (Q2) and trehalose octaacetate single HDC (Q1) solid dose forms respectively.

EXAMPLE 9

Figure 9:
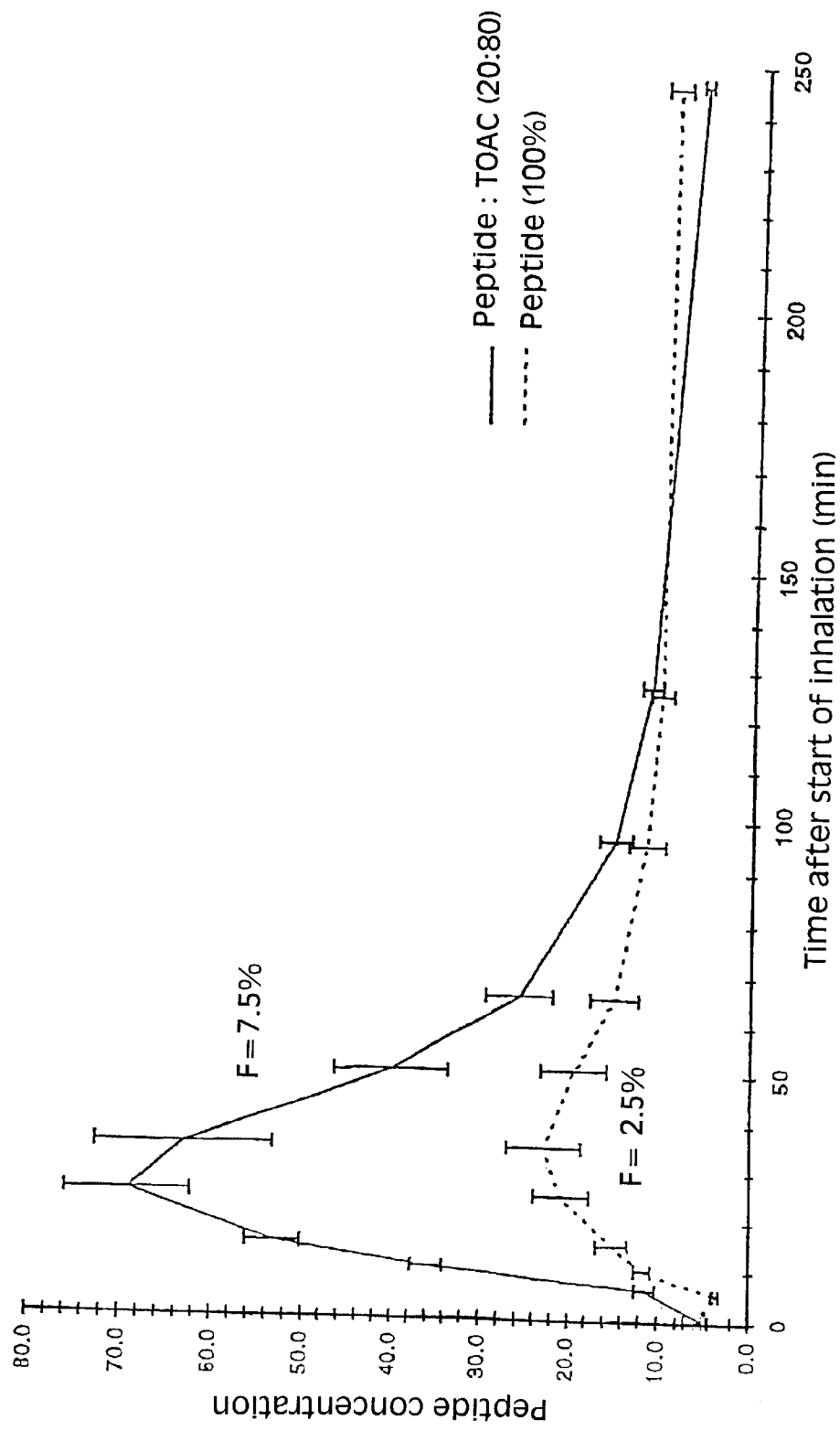
FIG. 9 is a graph depicting the bio-availability of pulmonary dosage of solid dose forms of insulin in the dog. The solid line represents the plasma levels of insulin detected on the pulmonary administration of the Q1 test formulation (vehicle of trehalose octaacetate containing 20% polypeptide). The dotted line represents the plasma levels of insulin detected on the pulmonary administration of the test polypeptide alone.

Bioavailability Study of the Pulmonary Delivery of a Solid Dose Form Containing Polypeptide in vivo A solid dose form containing the polypeptide hormone insulin was formulated (20% loading) in a trehalose octaacetate glass by solvent evaporation, by lyophilization of a 10% w/w solution of insulin and HDC in DMSO. The formulated glass was processed to give a fine powder of particle size 3–5 $\mu$m. The resulting solid dose form was administered at a dose of 1 i.u./kg to dogs using a Wright's dust feed apparatus for pulmonary delivery. The absorption of polypeptide was measured directly by immunoassay of blood insulin levels. The results obtained are shown in FIG. 9 and show increased pulmonary bioavailability of the HDC formulated polypeptide compared to the control administration of unformulated polypeptide (FIG. 9).

Although the foregoing invention has been described in some detail by way of illustration and example for purposes of clarity of understanding, it will be apparent to those skilled in the art that certain changes and modifications can be practiced. Therefore, the descriptions and examples should not be construed as limiting the scope of the invention, which is delineated by the appended claims.

We claim:

1. A pharmaceutical composition for pulmonary delivery comprising, an intimate mixture of a therapeutically effective amount of a bioactive agent, a surface active agent, and a hydrophobically derivatized carbohydrate (HDC) where the composition is in powder form and provides increased bioavailability of the bioactive agent to the pulmonary system wherein the surface active agent forms a continuous phase with the HDC.

2. The composition according to claim 1, wherein the surface active agent is a surfactant with a hydrophile-lipophile balance.

3. The composition according to claim 2, wherein the hydrophile-lipophile balance is of at least about 3.

4. The composition according to claim 3, wherein the surfactant is selected from the group consisting of glyceryl monostearate, sorbitan monolaurate, polyoxyethylene-4-lauryl ether, polyethylene glycol 400 monostearate, polyoxyethylene-4-sorbitan monolaurate, polyoxyethylene-20-sorbitan monopalmitate, polyoxyethylene-40-stearate, sodium oleate sodium lauryl sulfate and lung surfactants.

5. The composition according to claim 1, wherein mucosal delivery is via by-inhalation delivery.

6. The composition according to claim 1, wherein the powder contains particles with a size distribution of about 0.1 to 10 microns.

7. The composition according to claim 1, wherein the powder contains particles with a size distribution of about 0.5 to 5 microns.

8. The composition according to claim 1, wherein the powder contains particles with a size distribution of about 1 to 4 microns.

9. The composition according to claim 1, wherein the intimate mixture is obtained by dissolving or suspending the bioactive agent and the hydrophobically derivatized carbohydrate in at least one solvent therefor and evaporating the solvent from the mixture.

10. The composition according to claim 9, wherein the evaporating is by spray drying, freeze drying, air drying, vacuum drying, fluidized bed drying, co-precipitation, or super-critical fluid evaporation.

11. The composition according to claim 1, wherein the intimate mixture is obtained by combining the bioactive agent and hydrophobically derivatized carbohydrate, heating the mixture to obtain a melt of the carbohydrate and quenching the melt to form a glass.

12. The composition according to claim 1, wherein the powder is obtained by milling a glass.

13. The composition according to claim 1, wherein the bioactive agent is obtained from a class selected from the group consisting of anti-inflammatory bioactive agents, analgesics, antiarthritic bioactive agents, antispasmodics, antidepressants, antipsychotics, tranquilizers, antianxiety bioactive agents, narcotic antagonists, antiparkinsonism agents, cholinergic agonists, chemotherapeutic bioactive agents, immunosuppressive agents, antiviral agents, antibiotic agents, appetite suppressants, antiemetics, anticholinergics, antihistamines, antimigraine agents, coronary, cerebral or peripheral vasodilators, hormonal agents, contraceptives, antithrombotic agents, diuretics, antihypertensive agents, cardiovascular bioactive agents, and opioids.

14. The composition according to claim 13, wherein the bioactive agent is a hydrophobic molecule.

15. The composition according to claim 1, wherein the hydrophobically derivatized carbohydrate is selected from the group consisting of sorbitol hexaacetate (SHAC), α-glucose pentaacetate (α-GPAC), β-glucose pentaacetate (β-GPAC), 1-0-Octyl-β-D-glucose tetraacetate (OGTA), trehalose octaacetate (TOAQ, tetralose octapropionate (TOP), trehalose octa-3,3,dimethylbutyrate (TO33DMB), trehalose diisobutyrate hexaacetate, trehalose octaisobutyrate, lactose octaacetate, sucrose octaacetate (SOAC), cellobiose octaacetate (COAC), raffinose undecaacetate (RUDA), sucrose octapropanoate, cellobiose octapropanoate, raffinose undecapropanoate, tetra-0-methyl trehalose, trehalose octapivalate, trehalose hexaacetate dipivalate and di-0-methyl-hexa-0-actyl sucrose and mixtures thereof.

16. The composition according to claim 1, wherein the hydrophobically derivatized carbohydrate is a trehalose derivative and comprises:

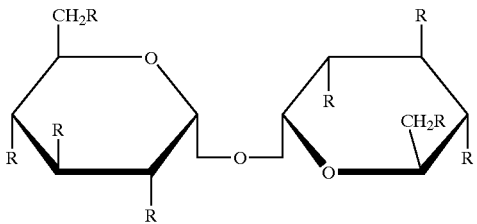

where R represents a hydroxyl group, or less hydrophilic derivative thereof, including an ester or ether or any functional modifications thereof where at least one R is not hydroxyl but a hydrophobic derivative; where functional modifications include where the oxygen atom is replaced by a heteroatom, such as N or S and where R can be of any chain length from $C_2$ upwards and can be straight, branched, cyclic or modified and mixtures thereof.

17. A composition comprising the powders of claim 1, suspended in an aqueous solution.

18. The composition according to claim 1, wherein the powder contains particles with a size distribution of 2.5–3 microns.

19. A composition for mucosal delivery comprising, an intimate mixture of a therapeutically effective amount of a bioactive agent, a surfactant with a hydrophile-lipophile balance of at least about 3 and a hydophobically derivatized carbohydrate where the composition provides increased bioavailability of the bioactive agent to the mucosal surface.

20. The composition according to claim 19, wherein the surfactant is selected from the group consisting of glyceryl monostearate, sorbitan monolaurate, polyoxyethylen-4-lauryl ether, polyethylene glycol 400 monostearate, polyoxyethylene-4-sorbitan monolaurate, polyoxyethylene-20-sorbitan monopalmitate, polyoxyethylene-40stearate, sodium oleate and sodium lauryl sulfate and lung surfactants.

21. The composition according to claim 19, wherein mucosal delivery is via gastrointestinal delivery.

22. The composition according to claim 19, wherein mucosal delivery is via ocular delivery.

23. The composition according to claim 19, wherein the intimate mixture is obtained by dissolving or suspending the bioactive agent, the surface active agent and the hydrophobically derivatized carbohydrate in at least one solvent therefor and evaporating the solvent from the mixture.

24. The composition according to claim 23, wherein the evaporating is by spray drying, freeze drying, air drying, vacuum drying, fluidized bed drying, coprecipitation, or super-critical fluid evaporation.

25. The composition according to claim 19, wherein the intimate mixture is obtained by combining the bioactive agent, surface active agent and hydrophobically derivatized carbohydrate, heating the mixture to obtain a melt of the carbohydrate and quenching the melt to form a glass.

26. The composition according to claim 19, wherein the bioactive agent is obtained from a class selected from the group consisting of anti-inflammatory bioactive agents, analgesics, antiarthritic bioactive agents, antispasmodics, antidepressants, antipsychotics, tranquilizers, antianxiety bioactive agents, narcotic antagonists, antiparkinsonism agents, cholinergic agonists, chemotherapeutic bioactive agents, immunosuppressive agents, antiviral agents, antibiotic agents, appetite suppressants, antiemetics, anticholinergics, antihistamines, antimigraine agents, coronary, cerebral or peripheral vasodilators, hormonal agents, contraceptives, antithrombotic agents, diuretics, antihypertensive agents, cardiovascular bioactive agents, and opioids.

27. The composition according to claim 26, wherein the bioactive agent is a hydrophobic molecule.

28. The composition according to claim 19, wherein the hydrophobically derivatized carbohydrate is selected from the group consisting of sorbitol hexaacetate (SHAC), α-glucose pentaacetate (α-GPAC), β-glucose pentaacetate (β-GPAC), 1-0-Octyl-β-D-glucose tetraacetate (OGTA), trehalose octaacetate (TOAC), trehalose octapropionate (TOP), trehalose octa-3,3,dimethylbutyrate (T033DMB), trehalose diisobutyrate hexaacetate, trehalose octaisobutyrate, lactose octaacetate, sucrose octaacetate (SOAC), cellobiose octaacetate (COAC), raffinose undecaacetate (RUDA), sucrose octapropanoate, cellobiose octapropanoate, raffinose undecapropanoate, tetra-0-methyl trehalose, trehalose octapivalate, trehalose hexaacetate dipivalate and di-0-methyl-hexa-0-actyl sucrose and mixtures thereof.

29. The composition according to claim 19, wherein the hydrophobically derivatized carbohydrate is a trehalose derivative and comprises:

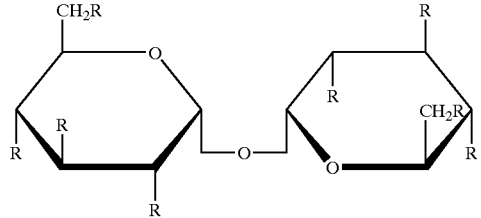

where R represents a hydroxyl group, or less hydrophilic derivative thereof, including an ester or ether or any functional modifications thereof where at least one R is not hydroxyl but a hydrophobic derivative; where functional modifications include where the oxygen atom is replaced by a heteroatom, such as N or S and where R can be of any chain length from $C_2$ upwards and can be straight, branched, cyclic or modified and mixtures thereof.

30. A composition according to claim 19, comprising the pharmaceutical composition in powder form, suspended in an aqueous solution.

* * * * *

UNITED STATES PATENT AND TRADEMARK OFFICE
CERTIFICATE OF CORRECTION

PATENT NO.    : 6,517,860 B1
DATED         : February 11, 2003
INVENTOR(S)   : Bruce Joseph Roser et al.

It is certified that error appears in the above-identified patent and that said Letters Patent is hereby corrected as shown below:

<u>Column 14,</u>
Line 50, "polyoxyethylene-40stearate, sodium oleate" should read -- polyoxyethylene-40-stearate, sodium oleate --.

Signed and Sealed this

Sixteenth Day of September, 2003

JAMES E. ROGAN
*Director of the United States Patent and Trademark Office*